(12) United States Patent
Lin et al.

(10) Patent No.: US 8,197,860 B2
(45) Date of Patent: Jun. 12, 2012

(54) METHOD FOR ENHANCING NUTRIENT ABSORPTION WITH ASTRAGALOSIDES

(75) Inventors: Hang-Ching Lin, Taipei (TW); Wen-Liang Chang, Taipei (TW); Tsu-Chung Chang, Taipei (TW); Hsiou-Yu Ding, Tainan (TW); Tian Shung Wu, Tainan (TW)

(73) Assignee: Nuliv Holding Inc., Taipei (TW)

( * ) Notice: Subject to any disclaimer, the term of this patent is extended or adjusted under 35 U.S.C. 154(b) by 69 days.

(21) Appl. No.: 12/424,193

(22) Filed: Apr. 15, 2009

(65) Prior Publication Data

US 2010/0099633 A1    Apr. 22, 2010

Related U.S. Application Data

(63) Continuation-in-part of application No. 11/426,029, filed on Jun. 23, 2006, now abandoned.

(60) Provisional application No. 60/694,097, filed on Jun. 23, 2005.

(51) Int. Cl.
*A61K 36/00* (2006.01)
*A61K 36/481* (2006.01)

(52) U.S. Cl. .................. 424/725; 514/909; 514/923

(58) Field of Classification Search .................. None
See application file for complete search history.

(56) References Cited

U.S. PATENT DOCUMENTS

| | | |
|---|---|---|
| 2007/0160693 A1 | 7/2007 | Zhong et al. |
| 2008/0113925 A1 * | 5/2008 | Harley et al. ............ 514/26 |

FOREIGN PATENT DOCUMENTS

| | | | |
|---|---|---|---|
| CN | 1245065 | | 2/2000 |
| CN | 1481805 A | * | 3/2004 |
| JP | 62012792 A | * | 1/1987 |

OTHER PUBLICATIONS

Lou et al, Determination of astragaloside I and elements in Guiqi prescription of blood nutrition capsule, Guangdong Weiling Yuansu Kexue (2002), 9(4): 47-49.*
Mitrache et al, Anemia: an indicator for malnutrition in the elderly, Ann Hematol (2001) 80: 295-298.*
Anonymous, Hepatitis C: nutrition care Canadian guidelines for health care providers, Canadian journal of dietetic practice and research, 2003; 64 (3): 139-41.*
Hamburger et al, Intestinal absorption and jejunal morphology in duodenal ulcer patients, with particular reference to the influence of subtotal gastric resection, American Journal of Digestive Diseases, 1963, vol. 8, No. 9, pp. 365-369.*
Chen, et al., "*Preparation of Astragalus injection and oral liquor and analysis of their ingredients*", Huaxue Shijie, 30(9): 391-3, 1989.
Gu, et al., "*Transport and bioavailability studies of Astragaloside IV, and active ingredient in Radix Astragali*", Basic & Clinical Pharmacology & Toxicology 2004, 95, 295-298.
Yang, et al., "*Effect of Astragalus membranaceus on myoelectric activity of small intestine*", Chinese Journal of Integrated Traditional and Western Medicine 13 (10): 617-7, 1993.

* cited by examiner

*Primary Examiner* — Quiwen Mi
(74) *Attorney, Agent, or Firm* — Occhiuti Rohlicek & Tsao LLP (57) ABSTRACT

The present application relates to a method for enhancing absorption of a nutrient in a subject in need thereof with an effective amount of an isolated astragaloside compound.

3 Claims, 4 Drawing Sheets

| | |
|---|---|
| Control | Rate = 6.3720 ± 1.9290 nmol/mg protein/min |
| 1 μM AS4 | Rate = 9.0020 ± 1.8300 nmol/mg protein/min |
| 0.1 μM AS4 | Rate = 10.460 ± 2.6690 nmol/mg protein/min |
| 0.01 μM AS4 | Rate = 11.670 ± 2.5800 nmol/mg protein/min |

*Fig. 1*

| | |
|---|---|
| Control | Rate = 10.6855 ± 0.2523 nmol/min |
| 0.1 µM AS1 | Rate = 15.7300 ± 1.1250 nmol/min |
| 0.01 µM AS1 | Rate = 16.2327 ± 0.7215 nmol/min |
| 0.001 µM AS1 | Rate = 14.2554 ± 0.5851 nmol/min |

*Fig. 2*

| | |
|---|---|
| Control | Rate = 8.9420 ± 0.3670 nmo/min |
| 1 µM AS1 | Rate = 16.000 ± 1.3190 nmol/min |
| 0.1 µM AS1 | Rate = 23.130 ± 1.3120 nmol/min |
| 0.001 µM AS1 | Rate = 22.220 ± 0.8695 nmol/min |

*Fig. 3*

Control              Rate = 53.140 ± 3.5540 pmol/mg protein/min 0.1 µM AS1           Rate = 79.710 ± 3.0410 pmol/mg protein/min

*Fig. 4*

METHOD FOR ENHANCING NUTRIENT ABSORPTION WITH ASTRAGALOSIDES

CROSS-REFERENCE TO RELATED APPLICATION

This application is a continuation-in-part of U.S. patent application Ser. No. 11/426,029, filed Jun. 23, 2006 (now abandoned), which claims the benefit of the priority pursuant to 35 U.S.C. §119(e) of U.S. Provisional Patent Application No. 60/694,097, filed Jun. 23, 2005. The contents of the prior applications are incorporated herein by their entireties.

BACKGROUND OF THE INVENTION

From the study of the human digestive system, it has been found that a huge variety of nutritional substances are obtained by breaking down and digesting the food in the gastrointestinal tract. The gastrointestinal tract is an important route by which the food is digested and absorbed. With regard to absorption, the nutritional substances, such as glucose, amino acids, vitamins and other smaller molecules are absorbed along the entire tract, either by diffusion or by specialized transport processes. Instead of moving freely across the intestinal membrane to the blood stream or lymph, most of these nutritional substances are transported by a tightly regulated mechanism. Based on current understanding in cell biology and physiology, the nutritional substances are transported across the cells with specific transport proteins and channels anchored on the cell membrane.

In the example of glucose transportation, almost all of the cells have a carrier-mediated mechanism for the transport of glucose from blood. For most cells, this transport occurs by facilitated diffusion using one or more of the glucose transporters (GLUT) in a family of facilitated glucose transporters. In these cases, net glucose transport occurs as a result of an inwardly directed chemical gradient for glucose. In a few cell types (e.g. those of intestinal mucosa and renal proximal tubule), uptake of glucose from an extracellular solution can occur against a gradient of glucose in a so-called active transport mechanism, thereby permitting net absorption of glucose from a tissue compartment whose glucose concentration may be lower than that of the blood. There are two ways in which a flow of energy can be coupled to transporters. The primary active transport requires energy be provided by adenosine triphophatase (ATPase). The secondary active transport provides energy from the flow of ions from an area of higher concentration to one of lower concentration.

According to the secondary active transport model described above, $Na^+$ binds to transport protein on the luminal side of the cell causing conformational change of the transport protein, which opens the binding site for glucose. Then, glucose binds to the transport protein. The transport protein that is bound with both $Na^+$ and glucose is subjected to further conformational change to allow entry of glucose and $Na^+$ into the cells. This active transport of glucose involves a direct physical coupling of flows of $Na^+$ and glucose, with the energy of the process being derived from the inwardly directed gradient for $Na^+$. Since the transport event includes a net movement of charge (the cationic $Na^+$ ion with the non-electrolyte glucose), the driving force for this uptake includes both the chemical gradient for $Na^+$ and the potential difference across the membrane. As the glucose gradually accumulates in the cell, it is subsequently transported out to the blood vessel via a glucose concentration gradient by facilitated diffusion. Similarly, other nutritional substances may be absorbed with the transport mechanism described above.

Astragalus root (*Radix Astragali*) has been used as a traditional Chinese medicine that mainly serves to invigorate the function of the spleen and increase stamina and endurance. Astragalus root (*Radix Astragali*) was found to enhance the immune system and help the human body resist virus infections, particularly in the lungs, by increasing production of interferon, an immune factor that inhibits viral growth. Astragalus root has been used as an adjuvant therapy in the treatment of colds and influenza. *Radix Astragali* was also reported to have effects on cardiovascular activity. Alcohol extracts of *Radix Astragali* enhanced both the contractility and contraction amplitude of isolated frog or toad hearts. Furthermore, astragalosides isolated from *Radix Astragali* have been reported to exert a positive inotropic effect on isolated rat hearts.

However, *Astragalus membranaceus* var. *mongholicus* has not been implied in regulating nutrient absorption and transportation. None of the study or research has focused on regulating the nutrient absorption using saponin compounds purified from Chinese herbal medicines, particularly *Astragalus membranaceus* var. *mongholicus*.

BRIEF SUMMARY OF THE INVENTION

The present invention provides a method for enhancing the absorption of a nutrient, such as glucose, an amino acid (e.g. arginine or tryptophan), and a vitamin (e.g., folate), in a subject in need thereof. This method includes the steps of identifying a subject who needs up-regulation of nutrient absorption and administering to the subject an effective amount of an isolated astragaloside compound (e.g., from *Astragalus membranaceus* var. *mongholicus*). "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents. Subjects in need of this regulation include elderlies, juveniles, pregnant or menopausal women, post-surgery patients, and patients suffering from long-term pressure, abnormal metabolism (e.g., type II diabetics), a weakened immune system (e.g., leukemia patients, HIV carriers, and organ transplantation recipients), or other diseases/disorders listed in Table 1 below.

The astragaloside compound, preferably isolated, is an cycloartane compound of Formula (A):

Formula (A)

wherein $R_1$ is selected from the group consisting of H, OH, O-acetyl, O-xylopyranosyl, O-(2-acetylxylopyranosyl), O-(3-acetylxylopyranosyl), O-(2,3-diacetylxylopyranosyl), O-(2,4-diacetylxylopyranosyl), O-xylopyranosyl-(1-2)-β-D-glucopyranosyl and O-xylopyranosyl-(1-2)-α-arabinopyranosyl; $R_2$ is selected from the group consisting of H, OH, O-acetyl and O-glucopyranosyl, O-xylopyranosyl; $R_3$ is selected from the group consisting of H, OH and O-acetyl; and $R_4$ is selected from the group consisting of The term "isolated astragaloside compound" used herein refers to an astragaloside compound prepared by a synthetic method or enriched from a natural source (e.g., *Astragalus membranaceus* var. *mongholicus*). For example, an isolated astragaloside compound is a preparation that contains at least 40% (e.g., at least 95%) of the astragaloside compound by dry weight. Purity of an isolated compound can be measured by, e.g., column chromatography, mass spectrometry, high performance liquid chromatography (HPLC), NMR, or any other suitable methods.

Preferably, the astragaloside compound used in the method of this invention is selected from the group consisting of astragaloside I of Formula I:

astragaloside II of Formula II:

astragaloside III of Formula III:

astragaloside IV of Formula IV:

Formula IV

Formula VI isoastragaloside I of Formula V:

Formula V astragaloside VI of Formula VI:

isoastragaloside II of Formula VII:

Formula VII and cycloastragenol-6-O-β-D-glucopyranose of Formula VIII:

Formula VIII

Additional features and advantages of the present invention will be set forth in part in the description which follows, and in part will be apparent from the description, or may be learned by practice of the invention. The features and advantages of the invention will be realized and attained by means of the elements and combinations as described.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments, which are presently preferred. It should be understood, however, that the invention is not limited to the precise arrangements and instrumentalities shown.

In the drawings:

FIG. 3 is a line graph showing the tryptophan absorption rates measured in the

Sink-transport across to basolateral chambers when the Caco2 monolayers were treated with the isolated astragaloside AS1 of Formula I of selected concentrations;

DETAILED DESCRIPTION OF THE INVENTION

To better understand the present invention, the terms used herein are explained in further detail. An astragaloside is defined as a triterpene saponin compound extracted from Radix Astragali, the dried root of *Astragalus membranaceus* (Fisch) Bunge and *Astragalus mongholicus* Bunge (Fabaceae).

As used herein, the singular forms "a", "an", and "the" include plural referents unless the context clearly dictates otherwise. Thus, for example, reference to "a compound" includes a plurality of such compounds.

The term "absorption" as used herein refers to uptake of a nutrient via a passage through the intestinal epithelium and into the blood or lymph.

The term "gut cells" as used herein generally include enterocytes, mucosal cell, and cells of intestinal epithelium responsible for nutrient absorption of the body.

The term "subject" as used herein refers to any animal, preferably including humans, where absorption of nutrients occurs across gut cells in the subject's gastrointestinal tract.

The present invention is based at least in part on the unexpected discovery that a number of astragaloside compounds enhance transportation of certain nutrients across a monolayer of the gut cells lining the gastrointestinal tract. See Examples 1-4 below. Thus, this invention provides a method for up-regulating the absorption of a nutrient with a astragaloside compound in a subject in need thereof. Table 1 below provides examples of the particular types of subjects who need enhanced absorption of particular nutrients:

TABLE 1

Subjects Who Need Up-Regulation of Absorption of Certain Nutrients

| Nutrient | Subject In Need |
|---|---|
| Glucose | Elderlies, athletes, alcoholics, juveniles, post-surgery patients, malnutrition patients, and patients having digestive tract disorders |
| Arginine | Juveniles, athletes, over-weight patients, patients suffering from cardiovascular disease, a weakened immune system, physical injury (e.g., burn trauma), and erectile dysfunction |
| Tryptophan | Over-weight patients, patients suffering from insomnia, a weakened immune system, and long-term pressure |
| Folate | Elderlies, pregnant women, nursing mothers, and patients suffering from insomnia, depression, cardiovascular disease, or long-term pressure |

The astragaloside compounds may be formulated into tablets, pills, capsules, liquid formulations and powder to be orally administered to the individual with nutrient absorption problem or mal-absorption syndrome, which is an alteration in the ability of the intestine to absorb nutrients adequately into the bloodstream. In one embodiment of the preparation of the liquid formulation, one or more of the astragaloside compounds may be dissolved in any solvent, preferably in a co-solvent, to produce a liquid formulation of the astragaloside compounds (such as, 10 mg of any of the astragaloside compounds may be dissolved in one mL of TRANSCUTOL® P [2-(2-ethoxyethoxy)ethanol]). Also, the astragaloside compounds may be optionally mixed with other nutrient factors, additives, stabilizing agents, carriers, binders and fillers to produce dietary supplements, beverages, food, and animal feeds for a subject in need of enhanced nutrient absorption. It may be apparent to one skilled in the art in view of the present disclosure to administer the astragaloside compounds in combination or in a cocktail manner with other ginsenosides and astragalosides to provide a synergistic or accumulative effect on the nutrient absorption.

The astragaloside compounds may be prepared by any standard methodology or known methods or knowledge in the art. According to the invention, the isolated astragaloside compounds, e.g., from *Astragalus membranaceus* var. *mon-*

*gholicus*, include the astragalosides. They may be isolated by other available extraction and isolation methods known to those skilled in the art. For example, the isolated astragaloside compounds may also be enriched from other Chinese herbal plants or vegetation to provide the same regulatory effect on nutrient absorption function. According to an embodiment of the invention, the astragaloside compounds may be obtained by a method comprising the steps of grinding the root of *Astragalus membranaceus* var. *mongholicus* and extracting with alcohol to produce an alcohol extract. The alcohol extract of *Astragalus membranaceus* var. *mongholicus* may be separated and purified to give seven known cycloartane compounds including astragaloside I (hereinafter "AS1") of Formula I:

astragaloside II of Formula II:

astragaloside III of Formula III:

astragaloside IV of Formula IV:

isoastragaloside I of Formula V:

Formula V astragaloside VI of Formula VI:

Formula VI and isoastragaloside II of Formula VII:

Formula VII

The cycloartane compounds may be separated and purified with silica gel and reversed phase chromatography. AS4 may further be hydrolyzed using naringinase to obtain a metabolite, such as cycloastragenol 6-O-β-D-gluco-pyranose (hereinafter "AA") of Formula VIII:

Formula VIII

In one embodiment, the absorption of glucose is enhanced by facilitating the transportation of glucose across the gut cells of the subject in need of the absoption enhancement with administration of one or more of the above-described astragaloside compounds at a concentration of about 0.001 µM to about 5 µM; wherein the astragaloside compound is AS1 of Formula I, AS4 of Formula IV, AS6 of Formula VI, IsoAS2 of Formula VII, or AA of Formula VIII.

In another embodiment, the absorption of arginine is enhanced by facilitating the transportation of arginine across the gut cells of the subject in need of the absorption enhancement with administration of one or more of the above-described astragaloside compounds at a concentration of about 0.001 µM to about 5 µM; wherein the astragaloside compound is AS1 of Formula I, AS2 of Formula II, AS3 of Formula III, AS4 of Formula IV, IsoAS1 of Formula V, AS6 of Formula VI, IsoAS2 of Formula VII, or AA of Formula VIII.

In still another embodiment, the absorption of tryptophan is enhanced by facilitating transportation of tryptophan across the gut cells of the subject in need of the absorption enhancement with administration of one or more of the above-described astragaloside compounds at a concentration of about 0.001 to about 5 µM; wherein the astragaloside compound is AS1 of Formula I, AS2 of Formula II, AS3 of Formula III, AS4 of Formula IV, IsoAS1 of Formula V, AS6 of Formula VI, IsoAS2 of Formula VII, or AA of Formula VIII.

In yet another embodiment, the absorption of folate is enhanced by facilitating transportation of folate across the gut cells of the subject in need of the absorption enhancement with administration of one or more of the above-described astragaloside compounds at a concentration of about 0.001 µM to about 5 µM; wherein the astragaloside compound is AS1 of Formula I, AS2 of Formula II, AS3 of Formula III, AS4 of Formula IV, IsoAS1 of Formula V, AS6 of Formula VI, IsoAS2 of Formula VII, or AA of Formula VIII.

The present invention is more specifically explained by the following examples. However, it should be noted that the present invention is not limited to these examples in any manner.

EXAMPLE 1

Regulatory Effects of Isolated Astragalosides on Glucose Uptake Cell Culture To evaluate the effect of the isolated astragaloside compound on the uptake of nutrient substances across the intestinal lumen, Caco-2 cells were grown on permeable filter as an experimental model. Caco2 cells originate from human colonic adenocarcinoma and spontaneously differentiate into an enterocyte-like phenotype after two weeks. The Caco-2 cell line, derived from a human colorectal carcinoma, has been used as an in vitro model system for studying drug absorption in gastrointestinal tract. These cells form monolayers with well-developed tight-junctions, and have been evaluated in details as an in vitro model to study both transcellular transport of nutrients and drugs in intestinal lumen.

Caco-2 cells were obtained from the ATCC (American Type Culture Collection). The cells were maintained in Dulbecco's modified Eagle medium (DMEM) containing 4.5 g/L glucose and 25 mM Hepes, supplemented with 10% fetal calf serum, 100 U/mL penicillin G and 10 µg/L streptomycin. The medium was changed every second day. The cells were routinely checked for Mycoplasma in monthly intervals. Caco-2 cells were cultured on semi-permeable membranes to differentiate into a highly functionalized epithelial barrier with remarkable morphological and biochemical similarity to the small intestinal columnar epithelium. The Caco-2 cell monolayers could therefore be used to study the membrane transport properties of many compounds. To trypsinize the cells, the culture dish was washed once with phosphate-buffered saline (PBS) followed by adding trypsine-EDTA for 10 minutes. The trypsinized cells were separated and filtered into single cells using a 35-µm strainer cap (Falcon 2235) before being seeded for further experiments.

Cell Viability Assay

To investigate whether the isolated astragalosides were toxic to the Caco2 cells, cell viability assay was carried out using culture medium supplemented with 1% and 10% FBS, respectively. The cells were seeded at a concentration of 5000 cells/well in a 96-well plate. To eliminate the boundary effect of the cell growth, the cells were only seeded in 60 wells of the middle area of the plate, whereas 36 wells at the surrounding area of the plate were filled only with 100 µL of PBS. Once the cells were attached to the plate, the cells were incubated in medium containing the isolated astragalosides at various doses (0, 1, 10, 20 and 50 µM). After 3 days, the culture medium was replaced with fresh medium containing the same compounds and incubated for 2 more days before the cells were assayed for cell viability.

The cell viability was determined by a Cell Counting Kit-8 (CCK-8, Dojindo Laboratories, Kumamoto, Japan) assay that is based on redox reaction of NADH in the living cells with cell proliferation reagent WST-8. WST-8 was reduced by dehydrogenases in electron transport chain (ETC) of mitochondria in the cells to give a yellow-colored formazan product, which was soluble in the tissue culture medium. The amount of formazan dye generated by the activity of dehydrogenases in the cells was directly proportional to the number of the living cells. Therefore, a greater light absorbance detected by ELISA reader at wavelength of 450 nm indicated presence of a larger number of the living cells.

The CCK-8 assay was carried out by adding 10 µL of the CCK-8 reagent in each well of 96-format plate. The plate was then covered with aluminum foil and further incubated for two hours before measuring for absorbance at wavelengths of 450 nm by using an ELISA reader.

Glucose Uptake Assay

Caco-2 cells ($5 \times 10^4$) were seeded in a 48-well plate and maintained in culture medium (DMEM with 10% FBS, 1% nonessential amino acids, L-glutamine, penicillin G (100 U/mL), streptomycin (10 µg/mL), and amphotericin B (2.5 µg/mL) in a 37° C. incubator for 10 days for the cells to differentiate. The culture medium was changed once every two days. The cells were then washed with PBS before replenishing with the culture medium containing 5% FBS and various astragalosides at the indicated concentrations (0.01, 0.1 and 1 µM) for 48 hours. The Caco2 cells were washed out of remaining glucose with PBS and replaced in the glucose buffer (80 mM NaCl, 100 mM mannitol, 20 mM Tris-HCl, pH 7.4, 3 mM $K_2HPO_4$, 1 mM $CaCl_2$, 1 mg/mL BSA) for 1 hour. Glucose uptake was initiated by replacing the glucose buffer with 0.2 ml of glucose buffer containing 2 µCi/mL of $^{14}C$-glucose and unlabeled cold glucose to give a final glucose concentration of 25 mM. Glucose uptake was stopped by removing the glucose buffer and washing with PBS at designated time intervals. The cells were lysed in 0.2 mL of 0.2 N NaOH, and 20 µL of the cell lysate were transferred to the filter-bottomed UniFilter plates (Perkin-Elmer, Wellesley, Mass., USA) and dried in a vacuum oven at 37° C. The bottom of the UniFilter plate was sealed and 25 µL of the counting solution were added into each well. Adhesive plate sealers were used in place of the lids and radioactivity of each sample was counted using the microplate liquid scintillation counter (TopCount, Packard NXT, Packard BioScience Company, Meriden, Conn., USA). The amount of glucose accumulated in the cells was calculated and normalized to protein concentration, and uptake rate was expressed as nanomoles of glucose per minutes per milligram of cell protein (nmol/min/mg). Protein concentration was determined by a standard Bicinchoninic acid (BCA) protein assay. Nonspecific glucose uptake was measured by adding 2 µCi of L-[$^{14}C$]-glucose and subtracting from each determination to obtain specific glucose uptake.

In the cell viability assay, the isolated astragaloside did not generally affect growth of Caco2 cells at a concentration range from 1 to 50 µM except when the AS1 of Formula I at a concentration of 10 µM was administered to Caco2 cells. Therefore, the isolated astragaloside was administered in the subsequent glucose uptake test or folate uptake test at a concentration range that did not cause cell toxicity. Preferably, the isolated astragaloside was administered at a concentration range of about 0.001 µM to about 1 µM.

Figure 1:
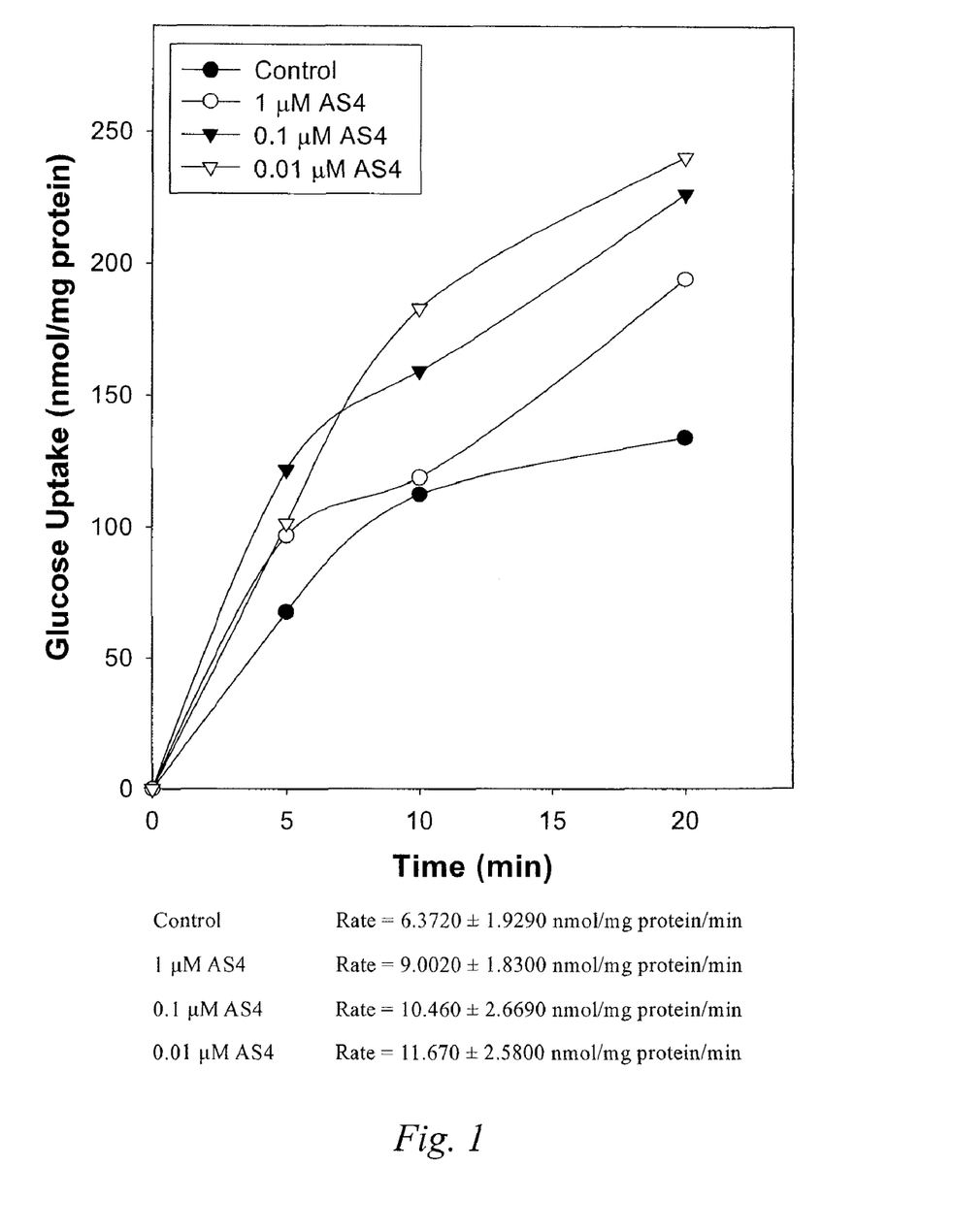
FIG. 1 is a line graph showing the glucose uptake rates of the Caco2 cells treated with the isolated astragaloside AS4 of Formula IV of selected concentrations.

From the glucose uptake assay shown in Table 2, it was found that isolated astragalosides, such as AS1 of Formula I, AS4 of Formula IV, AS6 of Formula VI, AA of Formula VIII, and IsoAS2 of Formula VII had regulatory effects on the glucose uptake of the Caco2 cells. The amount of glucose uptake was determined and expressed as "nmoles for each mg of cell protein". As shown in FIG. 1, the Caco2 cells treated with AS4 of Formula IV showed a much higher glucose uptake rate than the control group. The regulatory effects of the isolated astragalosides on the glucose transport in Caco2 cells are listed in Table 2 below, wherein the arrows that point up represent the enhancing effect on the glucose uptake.

TABLE 2

Regulatory effects of astragalosides on glucose uptake

| Compound (μM) | | Uptake rate (nmol/mg/min) | Percentage (%) | * |
|---|---|---|---|---|
| Control | | 6.3720 ± 1.9290 | 100 | — |
| AS1 | 1 | 6.2780 ± 1.9930 | 98.52 | |
| | 0.1 | 7.8260 ± 1.7510 | 122.82 | ↑ |
| | 0.01 | 9.3510 ± 1.1370 | 146.75 | ↑ |
| AS4 | 1 | 9.0020 ± 1.8300 | 141.27 | ↑ |
| | 0.1 | 10.460 ± 2.6690 | 164.16 | ↑ |
| | 0.01 | 11.670 ± 2.5800 | 183.15 | ↑ |
| AS6 | 1 | 7.8050 ± 1.1830 | 122.49 | ↑ |
| | 0.1 | 7.0070 ± 1.9470 | 109.97 | ↑ |
| | 0.01 | 7.6360 ± 1.7330 | 119.84 | ↑ |
| AA | 1 | 9.2830 ± 2.1150 | 145.68 | ↑ |
| | 0.1 | 9.3460 ± 2.3210 | 146.67 | ↑ |
| | 0.01 | 11.450 ± 3.2760 | 179.69 | ↑ |
| IsoAS2 | 1 | 6.1520 ± 2.4610 | 96.55 | |
| | 0.1 | 6.8210 ± 1.6630 | 107.05 | ↑ |
| | 0.01 | 7.3720 ± 2.5700 | 115.69 | ↑ |

It is concluded that the absorption of glucose can be enhanced by the astragaloside isolated from *Astragalus membranaceus* var. *mongholicus*, including AS1 of Formula I, AS4 of Formula IV, AS6 of Formula VI, AA of Formula VIII or IsoAS2 of Formula VII.

EXAMPLE 2

Regulatory Effect of Isolated Astragalosides on Arginine Absorption

Arginine Absorption Assay

In measuring transport of arginine across the Caco-2 cell monolayer, both sides of the transwells were washed with arginine incubation buffer consisting of: 137 mM NaCl, 10 mM Hepes, 0.3 mM $NaH_2PO_4$, 0.3 mM $K_2HPO_4$, 5.4 mM KCl, 2.8 mM $CaCl_2$, 1 mM $MgSO_4$, 10 mM glucose, adjusted to pH 7.4. Then, the cell layer was preincubated in the incubation buffer at 37° C. for 1 h. The volume of incubation buffer was 0.2 mL and 0.9 mL in the apical and basolateral chambers, respectively. The cells were replaced with fresh incubation medium in both chambers prior to the transport experiment. The transport experiment was initiated by replacing the incubation solution on the apical side with solution containing 10 mM of L-arginine in which 0.125 μCi/mL of L-[$^3$H]-arginine was included. At designated time intervals, 10 μL-solution samples were removed from the basolateral side and radioactivity of each sample was counted using a microplate liquid scintillation counter (TopCount, Packard NXT). During the experiment, when a 10 μL-solution sample was removed from the basolateral side every time, 10 μL buffer was supplemented to keep the volume constant. The uptake of [$^3$H]-mannitol was used to correct for nonspecific transport of molecules across the monolayer membrane. Results were expressed as the nanomoles of arginine transport across the Caco-2 cell monolayers with respect to time in minutes (nmol/min).

Figure 2:
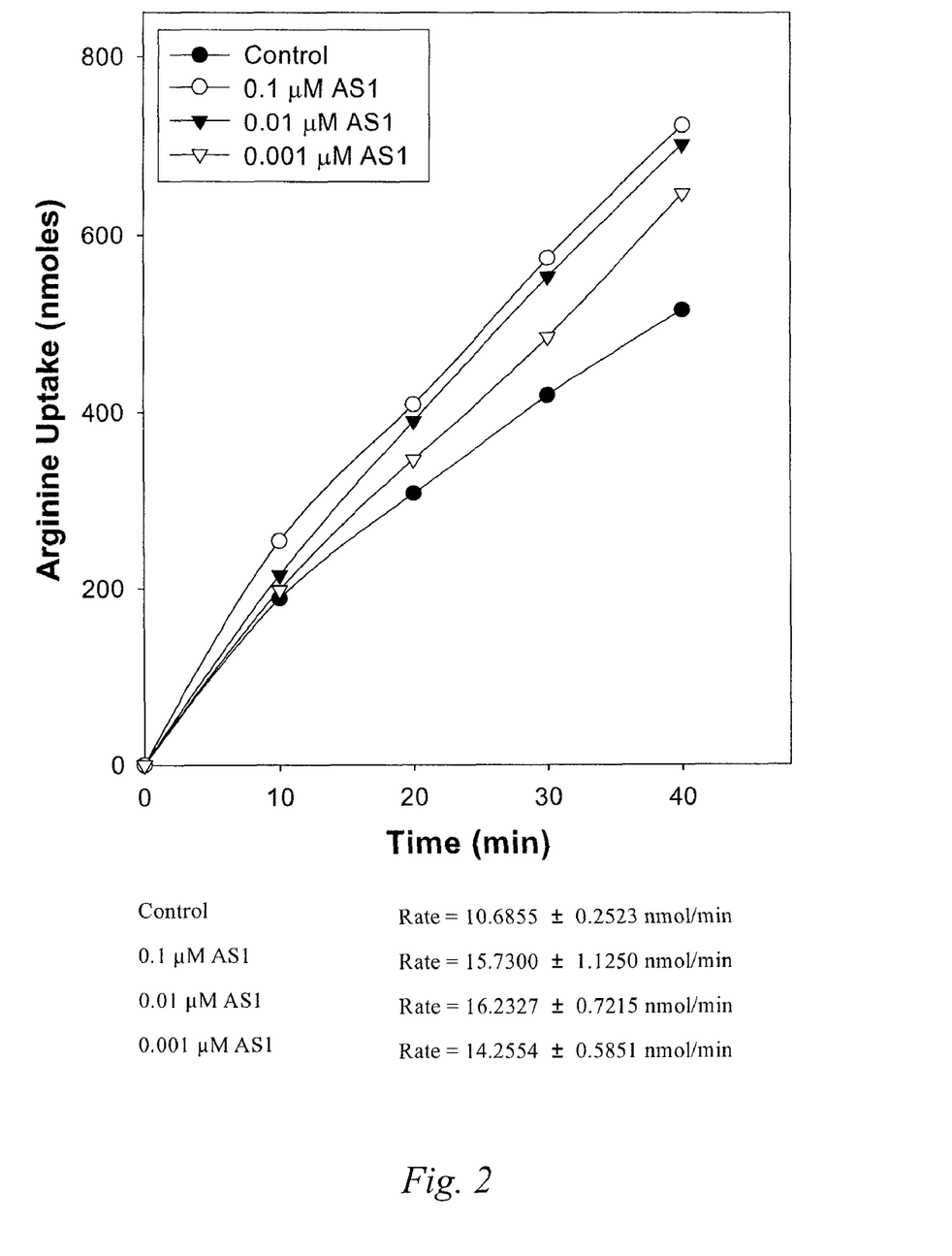
FIG. 2 is a line graph showing the arginine absorption rates measured in the Sink-transport across to basolateral chambers when the Caco2 monolayers were treated with the isolated astragaloside AS1 of Formula I of selected concentrations.

From the arginine absorption assay results shown in Table 3, it was found that isolated astragalosides, such as AS1 of Formula I, AS2 of Formula II, AS3 of Formula III, AS4 of Formula IV, AS6 of Formula VI, AA of Formula VIII, IsoAS1 of Formula V and IsoAS2 of Formula VII had regulatory effects on the arginine transport across the Caco2 cell monolayer. Referring to FIG. 2 and Table 3, the arginine transport rate was increased when the Caco2 cell monolayer was treated with AS1 of Formula I or AS2 of Formula II at a concentration from 0.001 μM to 0.1 μM. The arginine transport rate was increased when the Caco2 cell monolayer was treated with AS3 of Formula III, AS4 of Formula IV, AS6 of Formula VI, AA of Formula VIII, IsoAS1 of Formula V or IsoAS2 of Formula VII, respectively, at a concentration from 0.01 μM to 1 μM. The regulatory effects of the isolated astragalosides on the arginine transport in Caco2 cells are listed in Table 3 below, wherein the arrows that point up represent the enhancing effect on the arginine transport.

TABLE 3

Regulatory effects of isolated astragalosides on Arginine transport

| Compound (μM) | | Transport rate (nmol/min) | Percentage (%) | * |
|---|---|---|---|---|
| Control | | 10.6855 ± 0.2523 | 100 | — |
| AS1 | 0.1 | 15.7300 ± 1.1250 | 147.21 | ↑ |
| | 0.01 | 16.2324 ± 0.7215 | 151.91 | ↑ |
| | 0.001 | 14.2554 ± 0.5851 | 133.37 | ↑ |
| AS2 | 0.1 | 17.2771 ± 1.6170 | 161.69 | ↑ |
| | 0.01 | 16.2358 ± 1.6190 | 151.94 | ↑ |
| | 0.001 | 14.6355 ± 1.2910 | 136.97 | ↑ |
| AS3 | 1 | 15.8341 ± 1.0000 | 148.18 | ↑ |
| | 0.1 | 13.2858 ± 1.4110 | 124.33 | ↑ |
| | 0.01 | 13.0084 ± 1.0510 | 121.74 | ↑ |
| AS4 | 1 | 17.2241 ± 0.3759 | 161.19 | ↑ |
| | 0.1 | 18.4575 ± 0.5955 | 172.73 | ↑ |
| | 0.01 | 16.7245 ± 0.2890 | 156.52 | ↑ |
| AS6 | 1 | 13.5942 ± 1.2760 | 127.22 | ↑ |
| | 0.1 | 14.9986 ± 1.3200 | 140.36 | ↑ |
| | 0.01 | 13.9283 ± 1.7330 | 130.35 | ↑ |
| AA | 1 | 17.3164 ± 1.6150 | 162.06 | ↑ |
| | 0.1 | 18.2169 ± 1.8700 | 170.48 | ↑ |
| | 0.01 | 21.3347 ± 1.7800 | 199.66 | ↑ |
| IsoAS1 | 1 | 14.4734 ± 1.1350 | 135.41 | ↑ |
| | 0.1 | 21.3107 ± 1.5130 | 199.44 | ↑ |
| | 0.01 | 14.4776 ± 0.5519 | 135.49 | ↑ |
| IsoAS2 | 1 | 12.6518 ± 0.3680 | 118.40 | ↑ |
| | 0.1 | 14.1059 ± 0.1815 | 132.01 | ↑ |
| | 0.01 | 14.7577 ± 0.2837 | 138.11 | ↑ |

It is concluded that the absorption of arginine can be enhanced with the administration of astragalosides isolated from *Astragalus membranaceus* var. *mongholicus*, including AS1 of Formula I, AS2 of Formula II, AS3 of Formula III, AS4 of Formula IV, AS6 of Formula VI, AA of Formula VIII, IsoAS1 of Formula V or IsoAS2 of Formula VII.

EXAMPLE 3

Regulatory Effects of Isolated Astragalosides on Tryptophan Absorption

Trytophan Absorption Assay

The experimental procedures similar to those in Example 2 were used for measuring the uptake of tryptophan molecules across the Caco-2 membrane, except using a tryptophan incubation buffer consisting of 137 mM choline chloride, 10 mM Hepes, 0.6 mM $KH_2PO_4$, 5.4 mM KCl, 2.8 mM $CaCl_2$, 1 mM $MgSO_4$, and 10 mM glucose, and having its pH adjusted to 7.4. Results were expressed as the nanomoles of tryptophan transport across the Caco-2 cell monolayers with respect to time in minutes (nmol/min).

Figure 3:
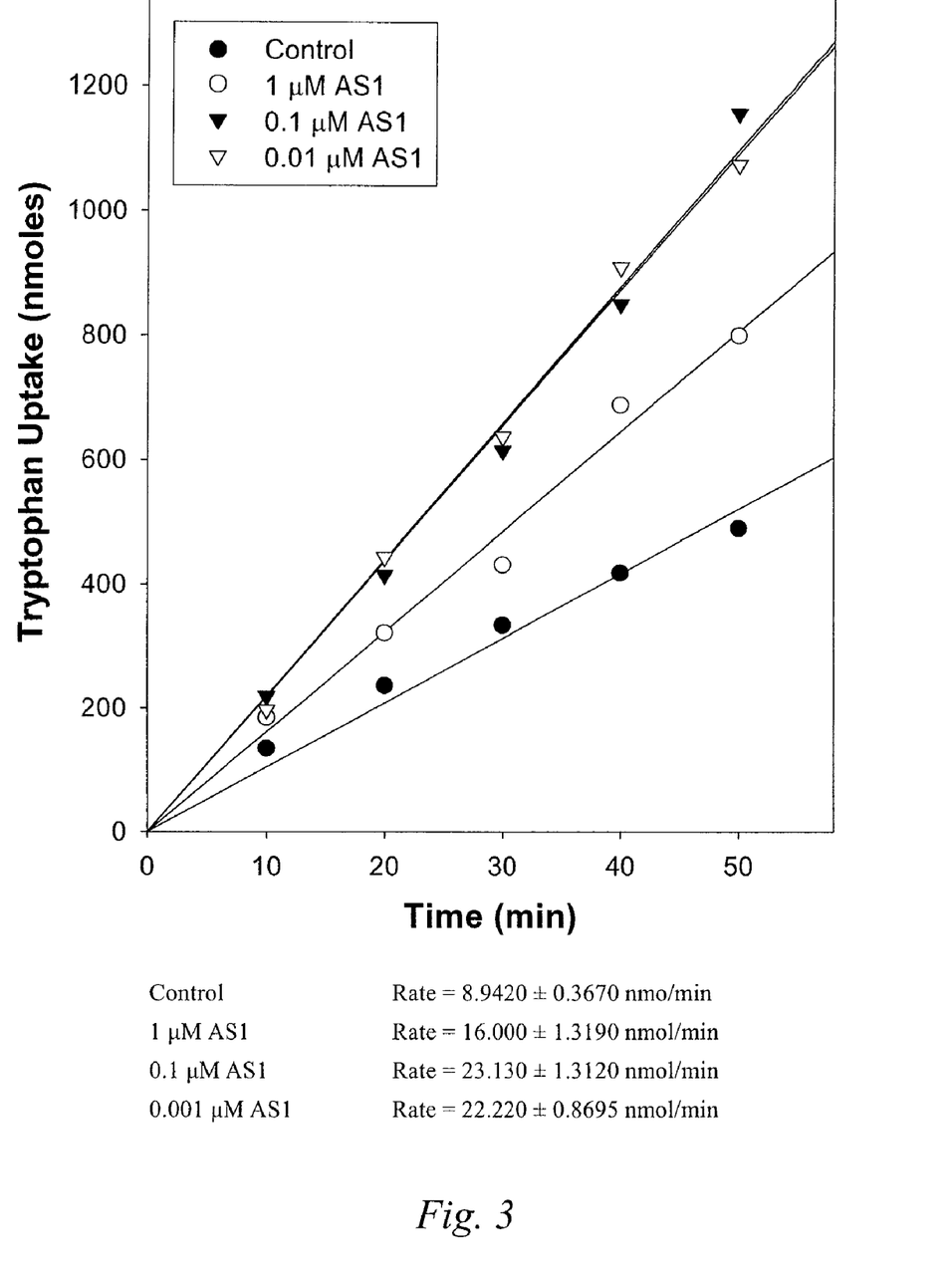

From the tryptophan absorption assay results shown in Table 4, it was found that isolated astragalosides, such as AS1 of Formula I, AS2 of Formula II, AS3 of Formula III, AS4 of Formula IV, AS6 of Formula VI, AA of Formula VIII, IsoAS1 of Formula V and IsoAS2 of Formula VII had regulatory effects on the tryptophan transport across the Caco2 cell monolayer. As shown in FIG. 3 and Table 4, the tryptophan transport rate was increased when the Caco2 cell monolayer was treated with AS2 of Formula II, AS3 of Formula III, AS4 of Formula IV, AS6 of Formula VI, AA of Formula VIII, IsoAS1 of Formula V or IsoAS2 of Formula VII respectively at a concentration from 0.01 μM to 1 mM, and with AS1 of Formula I at a concentration from 0.01 μM to 0.1 mM. The regulatory effects of the isolated astragalosides on the tryptophan transport in Caco2 cells are listed in Table 4 below, wherein the arrows that point up represent the enhancing effect on the tryptophan transport.

TABLE 4

Regulatory effects of isolated astragalosides on Tryptophan transport

| Compound (μM) | | Transport rate (nmol/min) | Percentage (%) | * |
|---|---|---|---|---|
| Control | | 8.9420 ± 0.3670 | 100 | — |
| AS1 | 1 | 16.000 ± 1.3190 | 178.93 | ↑ |
| | 0.1 | 23.130 ± 1.3120 | 258.67 | ↑ |
| | 0.01 | 22.220 ± 0.8695 | 248.49 | ↑ |
| AS2 | 1 | — | — | — |
| | 0.1 | 11.650 ± 0.5789 | 130.28 | ↑ |
| | 0.01 | 10.290 ± 0.4115 | 115.07 | ↑ |
| AS3 | 1 | 24.200 ± 1.0260 | 270.63 | ↑ |
| | 0.1 | 13.590 ± 1.0080 | 151.98 | ↑ |
| | 0.01 | 14.290 ± 1.3910 | 159.81 | ↑ |
| AS4 | 1 | 9.6640 ± 0.2770 | 108.07 | ↑ |
| | 0.1 | 12.730 ± 0.4470 | 142.36 | ↑ |
| | 0.01 | 10.130 ± 0.7025 | 113.29 | ↑ |
| AS6 | 1 | 15.490 ± 0.2161 | 173.23 | ↑ |
| | 0.1 | 13.850 ± 0.6567 | 151.87 | ↑ |
| | 0.01 | 15.510 ± 0.3688 | 173.45 | ↑ |
| AA | 1 | 12.100 ± 0.5197 | 135.32 | ↑ |
| | 0.1 | 14.000 ± 0.6445 | 156.56 | ↑ |
| | 0.01 | 11.900 ± 0.6231 | 133.08 | ↑ |
| IsoAS1 | 1 | 10.600 ± 0.8058 | 118.54 | ↑ |
| | 0.1 | 13.370 ± 0.3301 | 149.52 | ↑ |
| | 0.01 | 10.370 ± 0.8808 | 115.97 | ↑ |
| IsoAS2 | 1 | 20.070 ± 0.1931 | 224.45 | ↑ |
| | 0.1 | 13.060 ± 0.5530 | 146.05 | ↑ |
| | 0.01 | 13.000 ± 0.5547 | 145.38 | ↑ |

It is concluded that the absorption of tryptophan may be enhanced with the administration of the astragaloside isolated from *Astragalus membranaceus* var. *mongholicus*, including AS1 of Formula I, AS2 of Formula II, AS3 of Formula III, AS4 of Formula IV, AS6 of Formula VI, AA of Formula VIII, IsoAS1 of Formula V or IsoAS2 of Formula VII.

EXAMPLE 4

Regulatory Effects of Isolated Astragalosides on Folate Uptake

Folate Uptake Assay

The Caco2 cells were subjected to folate uptake test in a manner similar to that described in the glucose uptake assay in Example 1 above. In the folate uptake test, the Caco2 cells were pretreated with the culture medium containing 5% FBS and isolated astragalosides at a concentration of 0.1 μM for 2 days before the cells were cultured in a folate uptake buffer (Hank's balanced salt solution, supplemented with 0.14 g/L CaCl$_2$, 0.1 g/L MgCl$_2$, and 0.1 g/L MgSO$_4$, pH 6.0) for 1 hour. The buffer was then aspirated, and uptake was initiated by adding 0.2 mL of fresh folate uptake buffer containing 2 μCi/mL radioactive folate (3,5,7,9-$^3$H-folic acid, 25 mCi/mmol, ARC) and cold, unlabeled folate giving a final folate concentration of 5 μM. The folate uptake was terminated by removing the uptake buffer at designated time intervals. The cells were then washed three times with ice-cold PBS and lysed by the addition of 0.2 mL of 0.2N NaOH, followed by incubation at 65° C. for 20 min. Intracellular uptake of $^3$H-folate was determined by transferring 20 μL of the cell lysate to the filter-bottomed UniFilter plates (Perkin-Elmer) and counting as described previously in Example 1. The amount of folate accumulated in the cells was calculated and normalized to protein concentration, and uptake rate was expressed as picomoles of folate per minutes per milligram of cell protein (pmol/min/mg). Protein concentration was determined by a standard Bicinchoninic acid (BCA) protein assay as described above.

Figure 4:
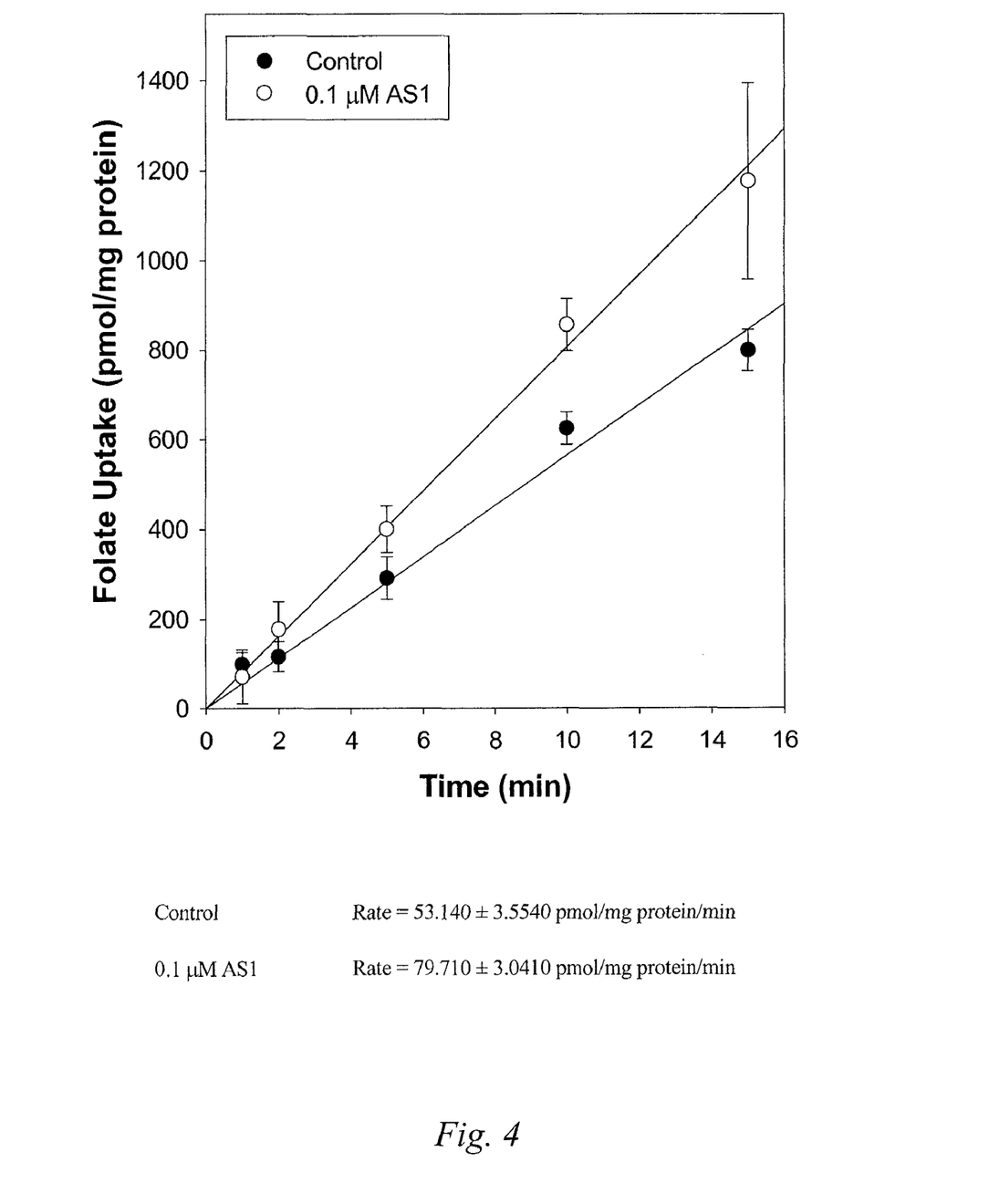
FIG. 4 is a line graph showing the folate uptake rates of the Caco2 cells treated with the isolated astragaloside AS1 of Formula I of a selected concentration.

Referring to FIG. 4, Caco2 cells treated with AS1 of Formula I at the concentration of 0.1 μM was found to exhibit an increased folate uptake from the control group having non-treated Caco2 cells. The regulatory effects of the isolated astragalosides on the folate uptake in Caco2 cells are listed in Table 5 below, wherein the arrows that point up represent the enhancing effect on folate uptake.

TABLE 5

Regulatory effects of isolated astragalosides on folate uptake

| | | Uptake rate (pmol/mg/min) | Percentage (%) | * |
|---|---|---|---|---|
| Control | | 53.140 ± 3.5540 | | — |
| 0.1 μM | AS1 | 79.710 ± 3.0410 | 150.00 | ↑ |
| Control | | 54.220 ± 3.1730 | | — |
| 0.1 μM | AS2 | 69.970 ± 3.7720 | 129.05 | ↑ |
| Control | | 55.280 ± 0.8527 | | — |
| 0.1 μM | AS3 | 80.380 ± 6.2170 | 145.41 | ↑ |
| Control | | 56.030 ± 0.9678 | | — |
| 0.1 μM | AS4 | 75.710 ± 5.2390 | 135.12 | ↑ |
| Control | | 60.240 ± 6.6510 | | — |
| 0.1 μM | AS6 | 84.560 ± 4.7200 | 140.37 | ↑ |
| Control | | 53.010 ± 6.3290 | | — |
| 0.1 μM | AA | 84.030 ± 4.9410 | 158.52 | ↑ |
| Control | | 50.720 ± 3.7550 | | — |
| 0.1 μM IsoAS1 | | 73.460 ± 3.6060 | 144.83 | ↑ |
| Control | | 53.19 ± 1.98 | | — |
| 0.1 μM IsoAS2 | | 86.63 ± 2.82 | 162.87 | ↑ |

It is concluded that the uptake of folate can be enhanced with the administration of the astragaloside isolated from *Astragalus membranaceus* var. *mongholicus*, including AS1 of Formula I, AS2 of Formula II, AS3 of Formula III, AS4 of Formula IV, AS6 of Formula VI, AA of Formula VIII, IsoAS1 of Formula V or IsoAS2 of Formula VII.

Although the above examples described regulating nutrient absorption of the colon cancer cells, it should be noted that the present invention is not limited as such. The gut cells and cells of gastrointestinal system should also be expected to benefit from the regulatory effect of the astragaloside compounds proposed in the present invention as long as these cells have similar nutrient transporting mechanisms. Besides a regulatory role in glucose, arginine, tryptophan and folate absorption, the astragaloside compounds described in the present invention may equivalently apply to regulate absorption of nutrients which include vitamins, amino acids, hormones, growth factors, and other elements important for cell metabolism. Moreover, the nutrient absorption test and nutrient uptake test described in the embodiments may be implemented interchangeably for assessing and evaluating the regulatory effect of the isolated astragaloside on the nutrient absorption of the individual according to the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for enhancing absorption of tryptophan in a subject in need thereof, comprising:
   identifying a human subject in need of enhanced absorption of tryptophan, and
   administering to the subject an effective amount of an isolated astragaloside compound for facilitating transportation of tryptophan across gut cells of the subject wherein the subject is an over-weight patient, a patient having insomnia, or a patient having long-term pressure.

2. The method of claim 1, wherein the astragaloside compound is an astragaloside compound of Formula (A):

Formula (A)

wherein $R_1$ is selected from the group consisting of H, OH, O-acetyl, O-xylopyranosyl, O-(2-acetylxylopyranosyl), O-(3-acetylxylopyranosyl), O-(2,3-diacetylxylopyranosyl), O-(2,4-diacetylxylopyranosyl), O-xylopyranosyl-(1-2)-β-D-glucopyranosyl, and O-xylopyranosyl-(1-2)-α-arabinopyranosyl; $R_2$ is selected from the group consisting of H, OH, O-acetyl, O-glucopyranosyl, and O-xylopyranosyl; $R_3$ is selected from the group consisting of H, OH, and O-acetyl; and $R_4$ is selected from the group consisting of 3. The method of claim 2, wherein the astragaloside compound is selected from the group consisting of astragaloside I of Formula I:

Formula I astragaloside II of Formula II:

Formula II astragaloside III of Formula III:

Formula III astragaloside IV of Formula IV:

isoastragaloside I of Formula V:

astragaloside VI of Formula VI:

isoastragaloside II of Formula VII:

Formula VII and cycloastragenol-6-O-β-D-glucopyranose of Formula VIII:

Formula VIII

* * * * *